United States Patent [19]

Carr

[11] Patent Number: 5,733,119
[45] Date of Patent: Mar. 31, 1998

[54] DENTAL RETRO-FILLING DRILL TOOL

[76] Inventor: Gary B. Carr, 11545 Sorrento Valley Rd., #313, San Diego, Calif. 92121

[21] Appl. No.: 423,745

[22] Filed: Apr. 17, 1995

[51] Int. Cl.⁶ .................................................. A61C 3/03
[52] U.S. Cl. ........................... 433/119; 433/102; 433/224
[58] Field of Search ................................. 433/119, 165, 433/224, 141, 166, 102

[56] References Cited

U.S. PATENT DOCUMENTS

| | | | |
|---|---|---|---|
| 1,067,015 | 7/1913 | Fowler | 433/102 |
| 3,133,351 | 5/1964 | Von Seggern | 433/119 |
| 3,703,037 | 11/1972 | Robinson | 433/96 |
| 4,330,278 | 5/1982 | Martin | 433/96 |
| 5,094,617 | 3/1992 | Carr | 433/119 |
| 5,320,530 | 6/1994 | Fong | 433/119 |

OTHER PUBLICATIONS

*Surgical Endodontics*, James L. Gutmann and John W. Harrison, 1991, Blackwell Scientific Publications, Inc., pp. 222–226.

*Primary Examiner*—John J. Wilson
*Attorney, Agent, or Firm*—Wood, Herron & Evans, L.L.P.

[57] ABSTRACT

Microsurgical drill bits for selective connection to an ultrasonic transducer head for use in dental retro-filling preparations each have a hub at one end for coupling to the transducer head, a cutting tip at the opposite end, and a shaft extending from the hub to the tip. The shaft has one or more steps in diameter at a predetermined position in its length designed for optimum vibration of the cutting tip without increasing the breakage rate above acceptable limits. The drilling tips have shafts which are angled relative to the hub and at least some have bent end portions so that the cutting tip is at an angle to the remainder of the shaft, allowing the transducer head to be held at a comfortable angle.

39 Claims, 2 Drawing Sheets

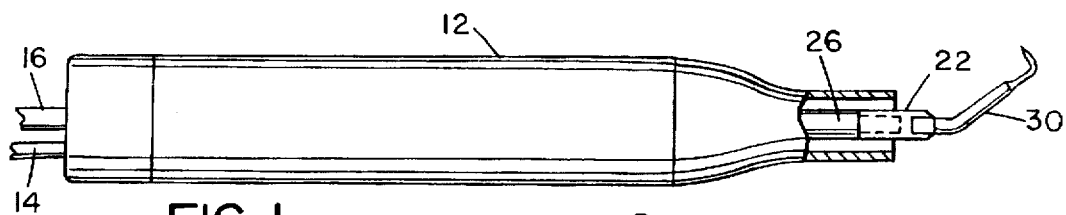
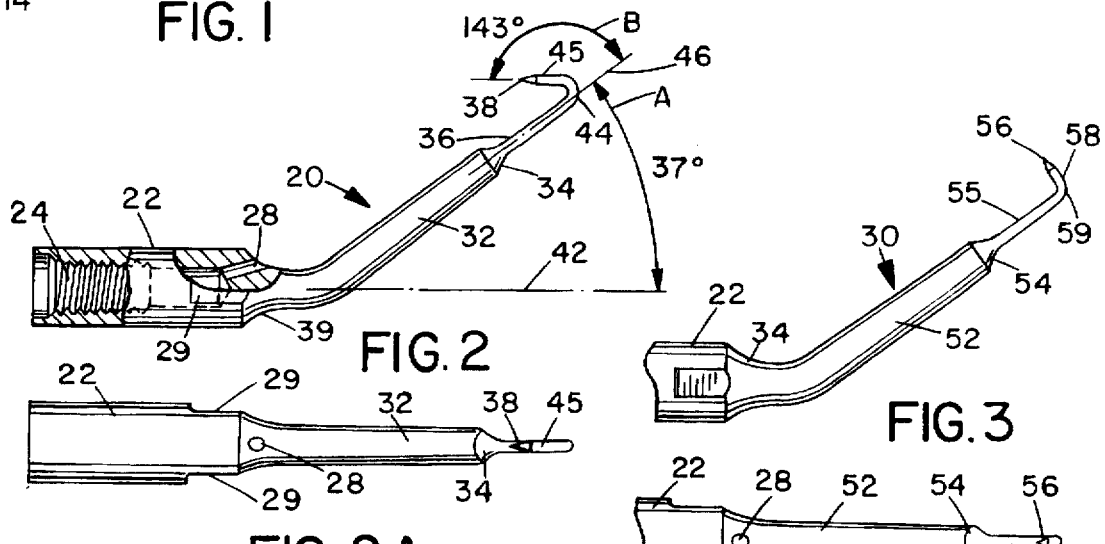
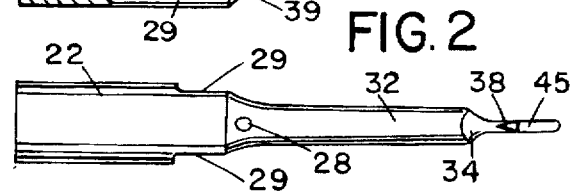
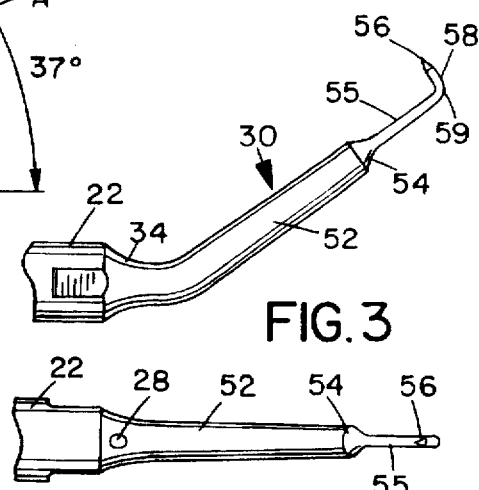
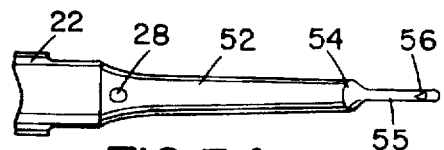
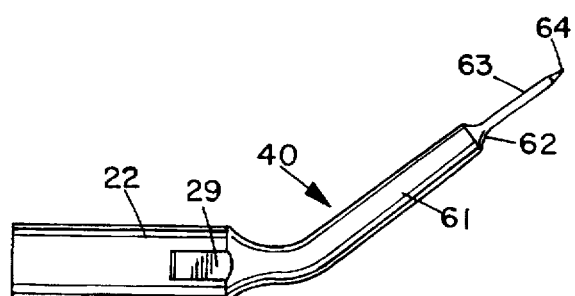
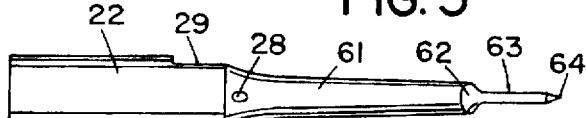
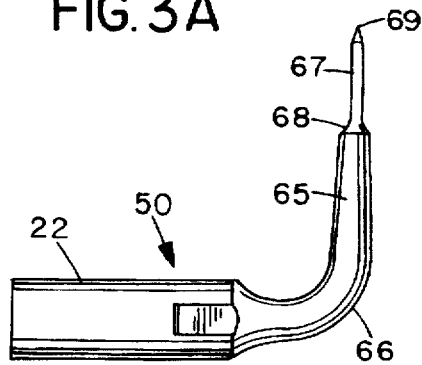
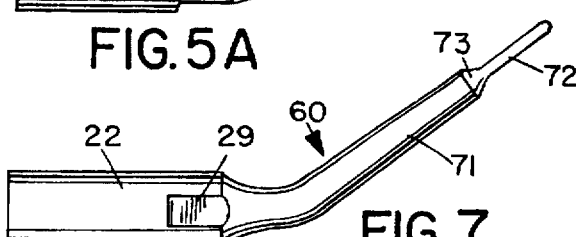
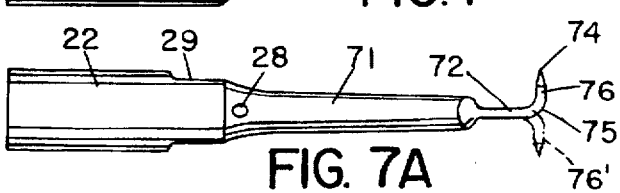
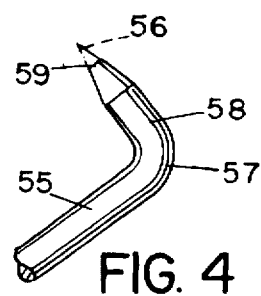

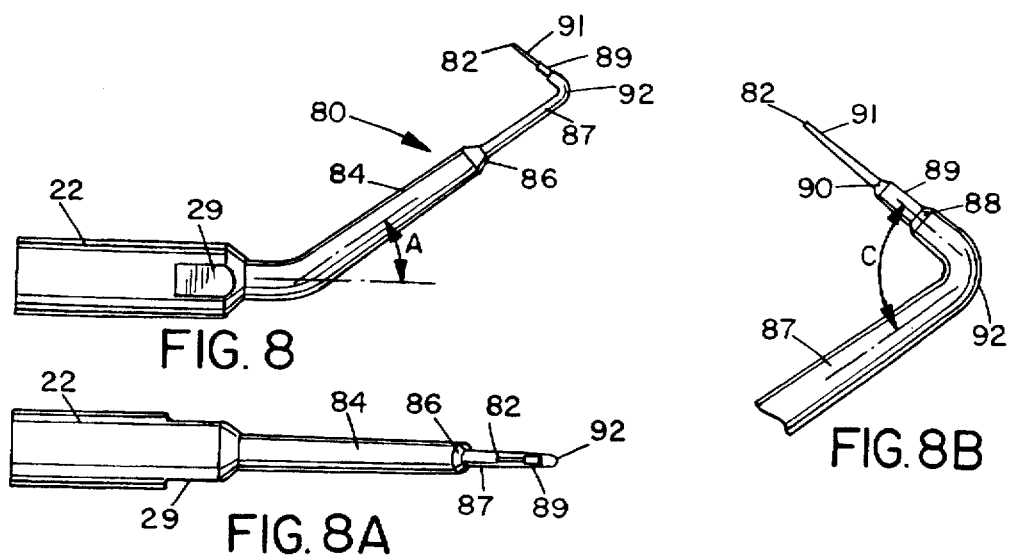
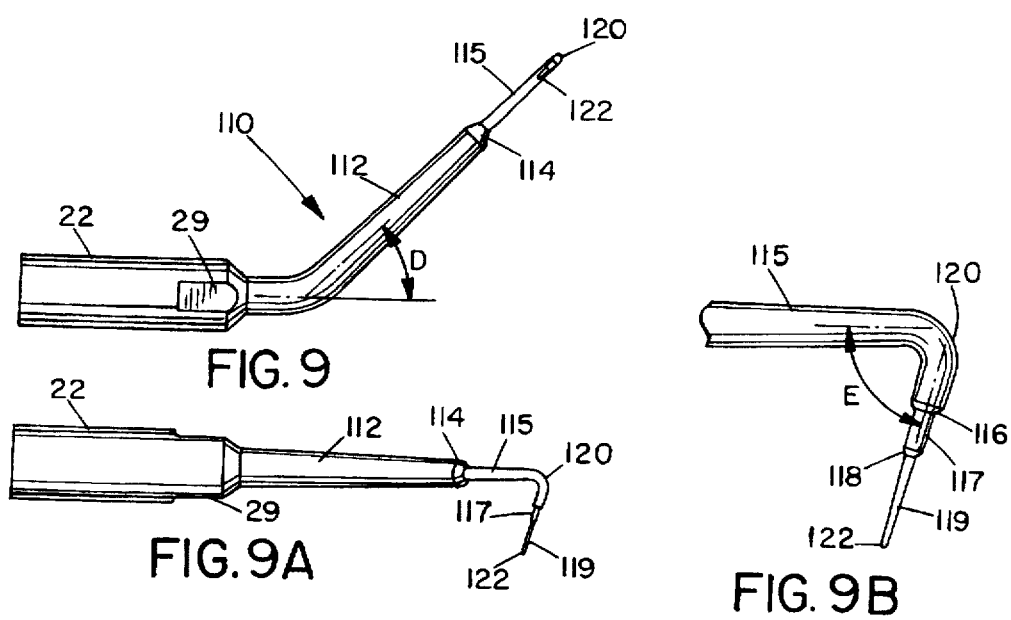
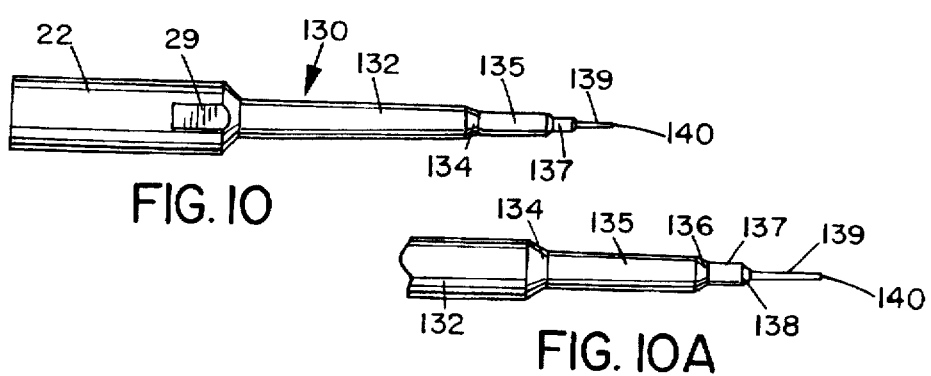

5,733,119

DENTAL RETRO-FILLING DRILL TOOL

BACKGROUND OF THE INVENTION

The present invention relates to drill tools or drill bits for use in preparation of dental retro-fillings, or drilling bores into the roots of teeth for receiving retro-fillings.

In root canal surgery, an opening is drilled into the tooth from the top, revealing the space in which the nerve is located. The nerve is then killed and the pulp removed, and the entire internal area is filled with a suitable filling material. However, this is sometimes not sufficient to deal with the problem, and the patient continues to feel pain in the tooth. In this event, the dental surgeon must drill into the bottom of the tooth root through the jawbone and remove the bottom of the tooth root, subsequently filling the drilled cylindrical bore with filling material. It is desirable to make the drilling through the jawbone and into the tooth root as small as possible to minimize trauma and risk of infection.

In my U.S. Pat. No. 5,094,617 entitled "Dental Retro-Filling Preparation Tool and Method," a tool for microsurgical dental retro-filling preparation was described in which a series of drill bits are provided, each with a hooked, pointed end portion in different orientations, and each of which may be selectively secured to an ultrasonic dental hand piece in order to drill a reverse cylindrical bore in a tooth root. The dentist determines the exact location and orientation of the root from X-rays, and drills a small hole in the jawbone at the appropriate location. The appropriate tip will be selected and attached to the transducer head, depending on the position and orientation of the tooth root, and the pointed end is then inserted through the drilled hole until the pointed end is aligned with the longitudinal axis of the root. The drill hand piece is then activated, so that the pointed end vibrates and cuts into the tooth root. Once the bore has been drilled to an appropriate depth, the tool is turned off and the bore can be filled appropriately. Each drill tip has an enlarged diameter end portion for releasably securing to the ultrasonic hand piece and an elongate shaft portion extending from the end portion and having a hooked, pointed end portion. The shaft portion of some tips is angled or curved, while others have a straight shaft. The hooked end portion may be co-planar with the end and shaft portion or offset. This allows an appropriate tip to be selected for easy access to a tooth root at any location and at different orientations or inclinations in the jaw, while still requiring only a small opening to be made in the jawbone. However, these drill tips have a tendency to break sometimes due to their small size and the amount of ultrasonic vibration transmitted to the tipped end of the tool, and in some cases the amount of vibration transmitted is relatively small.

SUMMARY OF THE INVENTION

It is an object of the present invention to provide a new and improved set of dental retro-filling drill tools.

According to the present invention, a dental retro-filling preparation tool is provided, which comprises an elongate drill bit having an enlarged hub at one end which has releasable coupling formations for releasably securing the drill bit to an ultrasonic transducer head, and an opposite, cutting end or tip for drilling into a tooth root, an extended shaft portion extending from the hub to the tip, the shaft portion having a step in diameter at a predetermined position in its length separating a first portion of a first diameter extending from the hub to the step in diameter from a second portion of a second diameter smaller than the first diameter extending from the hub to the tip. The position of the step is selected to provide an optimum amount of ultrasonic vibration to the tip while reducing the tendency for the tip to break off. In a preferred embodiment of the invention, the distance from the hub to the step in diameter is in the range from 0.5 to 0.6 inches, and preferably 0.55 inches.

The amount of vibration transmitted from the coupling at the hub to the tip of the drill bit is dependent on the mass in the shaft. More mass in the shaft results in more vibration transmitted to the tip. The enlarged diameter shaft portion therefore allows more vibration to be transmitted to the tip. However, if the step in diameter is positioned too close to the tip, it has been found that the vibration is too great, and the small tip will have a tendency to break off. If the step is too far away from the tip, the vibration is too low and the tip will not cut as well. The optimum position for the step is such that an optimum amount of vibration is transmitted to the tip without unduly increasing the risk of the tip breaking off during use. This position may be determined by appropriate testing of different step positions. Preferably, the step is at least 0.20 inches from the tip of the drill bit, as measured lengthwise along the shaft portion.

Preferably, a set of different drill bits is provided with tips at different orientations relative to the remainder of the drill bit, so that the dental surgeon can select an appropriate tip dependent on the location and orientation of the root to be drilled. The tip of the drill bit may be co-planar with the remainder of the tool or offset from the plane defined by the remainder of the shaft and hub, and may be aligned or coaxial with the remainder of the shaft or at various different angles to the remainder of the shaft. The first shaft portion may be coaxial with the hub in some drill bits and may be angled in other drill bits. A preferred set of drill bits comprises at least one drill bit with the tip aligned with the remainder of the shaft, at least one drill bit with the tip at an angle of 90° to the adjacent portion of the shaft, and at least one drill bit in which the tip is bent at an obtuse angle or angle greater than 90° to the adjacent portion of the shaft. At least some drill bits are provided in which the tip is offset relative to the plane in which the shaft and hub lie. This selection will permit a dental surgeon to select an appropriate drill bit for any root position and orientation, with the bit being readily aligned with the axis of the tooth root while the ultrasonic hand piece is still at a convenient orientation for comfortable gripping by the surgeon.

The drill bits of this invention provide more efficient cutting while reducing the tendency of the tip of the drill bit to break off during use. They permit the dental surgeon to align the tip readily along the axis of the tooth root, reducing the incidence of drilling offset cylindrical bores.

BRIEF DESCRIPTION OF THE DRAWINGS

The present invention will be better understood from the following detailed description of a preferred embodiment of the invention, taken in conjunction with the accompanying drawings, in which like reference numerals refer to like parts, and in which:

FIG. 1 illustrates a typical hand piece with a drill bit according to a preferred embodiment of the invention attached;

FIG. 2 is a side view of one preferred form of the drill bit, with portions cut away;

FIG. 2A is a top view of the drill bit of FIG. 2;

FIG. 3 is a side view of an alternative drill bit;

FIG. 3A is a top plan view of the drill bit of FIG. 3;

FIG. 4 is an enlarged view of a modified drill bit cutting end shape;

FIG. 5 is a side view of a further drill bit configuration;

FIG. 5A is a top view of the drill bit of FIG. 5;

FIG. 6 is a side view of a further form of the drill bit;

FIG. 7 is a side view of a further drill bit configuration;

FIG. 7A is a top view of the drill bit of FIG. 7;

FIG. 8 is a side view of another alternative drill bit configuration;

FIG. 8A is a top view of the drill bit of FIG. 8;

FIG. 8B is an enlarged view of the tip of the drill bit of FIG. 8;

FIG. 9 is a side view of a further drill bit configuration;

FIG. 9A is a top view of the drill bit of FIG. 9;

FIG. 9B is an enlarged view of the cutting end of the drill bit of FIG. 9;

FIG. 10 is a side view of another alternative drill bit configuration; and

FIG. 10A is an enlargement of the cutting end portion of FIG. 10.

DESCRIPTION OF THE PREFERRED EMBODIMENT

FIG. 1 of the drawings illustrates one drill bit 30 of a set of different drill bits secured to a typical ultrasonic dental hand piece or transducer head 12 of a type commonly used in conjunction with cleaning tips to remove calculus or plaque from teeth, crowns, fillings and the like. The transducer head 12 may, for example, comprise an Amadent ultrasonic unit or an Osada SE 04 ultrasonic transducer, or equivalent transducer heads containing a piezo-electric ultrasonic unit. These transducer heads have electrical input leads 14 and a water inlet 16 at one end, and a coupling device at the opposite end for suitably coupling the head to a selected drill bit.

FIGS. 2–7 of the drawings illustrate several alternative drill bits 20,30,40,50 and 60, respectively, which may be selectively coupled to transducer head or hand piece 12. In FIG. 1, drill bit 30 of FIGS. 3 and 3A is coupled to head 12, but it will be understood that any of the other drill bits may alternatively be coupled to head 12 as desired. The drill bits are all made from a suitable metal such as stainless steel, preferably 13-8 stainless steel. Each drill bit has an enlarged hub 22 at one end with a screw threaded bore 24 projecting inwardly from its end, as illustrated in FIG. 2, for releasable mating engagement with threaded shaft 26 forming the coupling device of head 12. Each of the drill bits will have an identical threaded bore to bore 24 illustrated in FIG. 2 for selective coupling with the head 12. Although in the illustrated embodiment the drill bits have threaded bores for coupling with a threaded shaft on the transducer head, it will be understood that drill bits may be provided with alternative coupling formations dependent on the type of head to which they are to be coupled, for example screw-threaded projections as described in my U.S. Pat. No. 5,094,617 may be provided for coupling with ultrasonic heads having threaded coupling bores. A water flow passageway or bore 28 is also provided between the bore 24 and the outer surface of the bit adjacent hub 22, for water flow to the drill tip. A pair of opposed flats 29 are provided on opposite sides of the hub for engagement with a wrench or the like for tightening the drill bit onto the head, and loosening it after a drilling operation is complete. The hub is identical on each of the drill bits, and like reference numerals have been used for like parts in FIGS. 3–7 as appropriate.

The drill bit 20 of FIGS. 2 and 2A has a first shaft portion 32 of a first diameter less than that of hub 22 extending from the hub up to a step 34, and a second shaft portion 36 of a second diameter less than that of shaft portion 32 extending from step 34 up to a tip or pointed end 38 of the bit. The tip 38 may be a sharp point or may be slightly rounded. Both shaft portions 32,36 are solid, not hollow. The transition 39 from hub 22 to shaft portion 32 is tapered or curved. The step 34 is also tapered. First shaft portion 32 is bent at a first angle A to the axis 42 of hub 22. The second shaft portion 36 also has a bend 44 adjacent tip 38 which bends the end portion 45 at an angle B relative to the axis 46 of the remainder of the shaft. In one example, the angle A for drill bit 20 is between 35° and 39°, preferably around 37°, while the angle B is greater than 90°, and is preferably between 141° and 145°, suitably around 143°. The tipped or bent end portion 45 is co-planar with the remainder of the drill bit, as best illustrated in FIG. 2A.

The drill bit 30 of FIGS. 3 and 3A has a first shaft portion 52 of a first diameter equivalent to that of first shaft portion 32 of the previous embodiment. Shaft portion 52 extends up to tapered step 54. A second shaft portion 55 of diameter less than that of shaft portion 52 extends from step 54 up to tip or pointed end 56, which also may be either a sharp point or slightly rounded. FIG. 4 illustrates a modified tip 59 for drill bit 30 which is flat. Preferably, drill tip 30 is provided in two alternatives, one with pointed tip 56 and one with flattened tip 59. The first shaft portion 52 is bent at an angle A identical to that of the drill bit 20, preferably around 37°. The second shaft portion 55 has a bend 57 adjacent tip 56, and the bent end portion 58 is oriented at an angle B of between 88° and 92°, preferably around 90° to the remainder of the shaft. As in the previous embodiment, the bent end portion 58 is co-planar with the remainder of the shaft.

FIGS. 5 and 5A illustrate another drill bit 40 of the set. As in the previous alternatives, drill bit 40 has a first shaft portion 61 of a first diameter extending from hub 22 up to step 62, and a second shaft portion 63 of a second diameter less than the first diameter extending from step 62 up to tip 64. As in the first two alternatives, the first shaft portion 61 is bent at an angle A to the axis of hub 22, and angle A is preferably around 37° as in FIGS. 2 and 3. The second shaft portion 63, unlike the previous alternatives, has no bend, and is coaxial with the first shaft portion up to the tip.

The drill bit 50 of FIG. 6 has a first shaft portion 65 which is bent at bend 66 at a right angle to the hub 22. The second shaft portion 67 of reduced diameter extends from step 68 up to tip 69, and is coaxial with shaft portion 65 up to the tip, as in the previous embodiment.

FIGS. 7 and 7A illustrate an alternative drill bit 60 which is similar to drill bit 30 of FIG. 3 but has an offset tip, unlike drill bit 30. Drill bit 60 has a first shaft portion 71 extending from hub 22 which is at an angle A of around 37° to hub 22, and a second shaft portion 72 of reduced diameter extending from step 73 up to tip 74. Second shaft portion 72 has a bend 75 adjacent tip 74 which bends end portion 76 so that it is inclined at an angle of 90°±2° to the remainder of the shaft, and is bent or offset out of the plane of the remainder of the shaft. Preferably, drill bit 60 is made in both a left hand version, illustrated in solid outline in FIG. 7A, in which bent end portion 76 is bent to the left of the remainder of the shaft, and a right hand version, illustrated in dotted outline in FIG. 7A, in which bent end portion 76' is bent to the right of the remainder of the shaft.

FIGS. 8–10 illustrate some other alternative drill bit configurations in which the shaft has a second step in diameter and is more tapered, allowing more vibration to be transmitted to the tip. This permits a greater angle to be provided on the tip without unduly increasing the risk of the tip breaking off in use. The drill bits of FIGS. 8–10 are otherwise identical to those of FIGS. 1–7, and like reference numerals have been used for like parts as appropriate.

FIGS. 8, 8A and 8B illustrate a drill bit 80 having a hub 22 for connection to an ultrasonic drill head as in the previous embodiments, and an elongate shaft with a pointed tip or drilling end 82. The shaft includes a first shaft portion 84 extending from the hub up to a first step in diameter 86, a second, reduced diameter shaft portion 87 extending from step 86 to a second step in diameter 88, a third shaft portion 89 of reduced diameter extending from step 88 up to a third step in diameter 90, and a fourth, end portion 91 extending from step 90 to the tip or cutting end 82. The first shaft portion 84 is bent at a first angle A of 37° to the axis of the hub 22, and the second shaft portion 87 has a bend 92 which bends the remainder of the shaft up to tip 82 at an angle C of around 75° to the first shaft portion 84 and axial part of shaft portion 87. The bent end portion of the shaft is coaxial with the remainder of the drill bit, as best illustrated in FIG. 8A.

By providing more steps in diameter and increasing the diameter of the shaft to a location closer to the cutting tip, the amount of vibration transmitted to the tip can be increased. The tip 82 is a flat or butt tip rather than a pointed tip, as illustrated in FIG. 8B. The design of the shaft with three successive steps in diameter has been found to significantly increase the cutting accuracy and provides a more aggressive cutting action. Additionally, by locating the bend 92 in the relatively large diameter shaft portion 87, the shaft can be bent through a greater angle without breaking. Although angle C is 75° in the illustrated embodiment, the drill bit 80 may be provided with tips having different back angles less than 90°.

FIGS. 9, 9A and 9B illustrate another modified drill bit 110 which also has a series of three steps in diameter in the shaft. The drill bit 110 of FIG. 9, 9A and 9B has a first shaft portion 112 of a first diameter extending from hub 22 up to a first step in diameter 114, a second shaft portion 115 extending from step 114 up to a second step in diameter 116, a third shaft portion 117 extending from step 116 up to third step in diameter 118, and a fourth reduced diameter shaft portion extending from step 118 up to cutting tip 120. In this embodiment, the first shaft portion 112 is bent at an angle D of around 45° to the axis of hub 22, and the second shaft portion 115 has a bend 120 which bends the remainder of the shaft extending up to tip 122 at an angle E of around 75° to the first part of the shaft. As best illustrated in FIG. 9A, the bent end portion of the shaft is bent out of the plane of the remainder of the shaft and hub, as in the drill tip of FIGS. 7 and 7A. Drill tip 110 may also be made in both a left hand and right hand version.

The angle E may be any back or reverse angle of less than 90°. The drill bit 110 also has a flat, non-pointed cutting end 122. As in the previous embodiment, the provision of three successive steps in diameter up to a location close to the cutting tip has been found to provide a more aggressive cutting action and also improves cutting accuracy. The location of bend 120 in relatively large diameter shaft portion 115 allows a sharper bend with a back action angle to be made without the tip breaking off, as would be likely to occur if such a bend were made in the minimum diameter end portion of the shaft.

FIGS. 10 and 10A illustrate another modified drill bit 130 in which the shaft is coaxial with the hub up to the tip. As in the two previous embodiments, the shaft has three successive steps in diameter for increased cutting efficiency. Drill bit 130 has a first shaft portion 132 extending from the hub 22 up to a first step in diameter 134, a second shaft portion 135 extending from step 134 up to a second step in diameter 136, a third shaft portion 137 extending from step 136 up to a third step in diameter 138, and an end portion 139 extending from step 138 up to cutting tip 140. As best illustrated in FIG. 10A, the cutting tip 140 is flat and non-pointed.

Thus, each of the alternative drill bits includes an enlarged diameter shaft portion which extends over a major portion of the length of the shaft from the hub to the tip or pointed end of the drill bit, but terminates short of the tip such that an optimum amount of ultrasonic vibration can be transmitted to the tip, in other words enough to provide efficient cutting at the tip without unduly increasing the risk of the tip breaking off in use. The optimum position for the step in diameter between the first and second shaft portion in the versions of FIGS. 1–7 was determined by extensive testing. If the step is located too far away from the tip or pointed end of the drill bit, the tip will not cut as well since the vibrations transmitted to the tip will be reduced. On the other hand, if the step is located too close to the tip, the amount of vibration transmitted to the tip will be so high that the tip will tend to break off too frequently. Therefore, a position was determined at which the cutting efficiency was increased to the maximum amount possible without producing an unacceptably high rate of tip breakage, in other words where the breakage rate was less than 2%. As illustrated in the drawings, this position is located more than halfway along the length of the shaft portion from the hub to the tip. Preferably, the length of the first shaft portion is in the range from ⅗ to ⅘ of the length from the hub to the tip of the bit, while the length of the second shaft portion from the step to the tip is from ⅖ to ⅕ of the total length.

In the alternative versions of FIGS. 8–10, three successive steps in diameter are provided. This allows the change in diameter to be more gradual, and permits a larger diameter to be maintained closer to the tip. As noted above, it also permits sharper, back angle bends to be made in the shaft. The set of drill bits illustrated in FIGS. 8–10 will provide more aggressive cutting and improved accuracy. The length of the first shaft portion in FIGS. 8–10 is about the same as that of FIGS. 1–7, but the change in diameter at the end of the first shaft portion is much less in the successively stepped shafts of FIGS. 8–10.

The drill bits of this invention are very small and are designed for use in dental microsurgery, in which a microscope and video camera are used for accurate alignment of the tool during surgery. In one example of a set of drill bits as illustrated in FIGS. 1–7 of the drawings, the drill bit hub diameter was around 0.156 inches, and the first shaft portion had a diameter which tapered slightly along its length from the hub to the step, from a diameter of 0.086 inches to 0.063 inches. The second shaft portion had a diameter which also tapered slightly along its length from the step to the tip, from a diameter of 0.0219 inches to a diameter of 0.070 to 0.090 inches. The total length of the drill bit in FIG. 2 was 1.29 inches, while the total length of each of the drill bits in FIGS. 3–7 was around 1.18 inches. The length of the hub of each drill bit in FIGS. 2–7 was 0.40 inches, the length of the first shaft portion from the hub to the step was 0.55 inches, and the length of the second shaft portion from the step to the tip was around 0.34 inches for the drill bit of FIG. 2 and 0.23 inches for the drill bits of FIGS. 3–7. The length of the bent end portion of the drill bit in FIG. 2 was 0.107 inches, while the length of the bent end portion of the tip in FIGS. 3 and 7 was around 0.06 inches. The length of the bent end portion of the drill bit with a flattened tip 59, as illustrated in FIG. 4, was slightly less than that of FIG. 3, typically around 0.05 inches. The length of the bent end portions is dependent on the length of the bore to be drilled.

The small size of the drill bits significantly reduces the amount of trauma involved in preparation of a retro-filling bore in a tooth root, and thus also reduces the risk of infection. The dimensions used are designed to provide an optimum amount of vibration for efficient cutting at the tip without producing an unacceptably high risk of the tip breaking off in the patient's jaw during use. Where 13-8 stainless steel is the material used for the tips, these dimensions have been found to provide a breakage rate of no more than 2%. Alternative dimensions may be used as long as the diameter and length proportions between the first and second shaft portions remain substantially the same. In other words, the ratio of the diameter of the first shaft portion to that of the second shaft portion should be in the range from 3:1 to 4:1. The ratio of the length of the first shaft portion to that of the second shaft portion should be in the range from 1.5:1 to 2.5:1.

The various drill bits illustrated in the drawings provide a set of drill bits for use in dental retro-filling preparation in which a bore is drilled axially into the end of a tooth root. The bore is subsequently filled with a suitable filling material. The drill bit 30 of FIG. 3, one of the two alternative drill bits 60 (right hand or left hand offset) of FIGS. 7 and 7A, or one of the drill bits 90 or 110 of FIGS. 8 and 9, respectively, will first be attached to the transducer head 12. The drill bit to be used will be dependent on which drill bit provides the most comfortable hand position for the user during drilling. The selected drill bit 30,60,90 or 110 is used to make the initial cut in the tooth root and is a primary drill bit.

The drill bit 20 may subsequently be used if necessary, if the angle of the initially drilled bore is found to be non-axial with the root, or offset, on microscope inspection. Drill bit 20 may then be used to change the angle of the bore.

Finally, a drill bit with a flattened tip 59, as illustrated in FIG. 4, is used to flatten the end or floor of the drilled bore into the desired, box-like end shape.

Drill bit 40 of FIG. 5 or drill bit 130 of FIG. 10 may be used to uncover calcified canals which sometimes occur in tooth roots which have become decayed or damaged, or to remove broken instruments. Drill bits 40 and 130 are much smaller than the conventional burr used for such operations, and therefore cause considerably less trauma. In order to remove a broken instrument, drill bit 40 or 130 is attached to the transducer head and then used to make a groove around the broken instrument tip. The tip of the drill bit is then applied to the broken part, causing it to vibrate up through the previously formed groove so that it can be extracted.

The drill bits of this invention are designed to provide an optimum amount of vibration at the drill tip while maintaining an acceptable breakage rate of no more than 2%. Due to their small size, they produce minimal trauma when used for dental retro-filling preparations, while still producing sufficient cutting for readily drilling bores in tooth roots. The different angle tips allow an appropriate drill bit to be selected such that the angle at which the transducer head or hand piece must be held is comfortable.

Although some preferred embodiments of the invention have been described above by way of example only, it will be understood by those skilled in the field that modifications may be made to the disclosed embodiments without departing from the scope of the invention, which is defined by the appended claims.

I claim:

1. A dental retro-filling preparation tool of increased overall taper for use with an ultrasonic dental hand piece, comprising:

an elongate drill bit having at an inner end a hub with a longitudinal axis and a releasable coupling formation connectable to an ultrasonic dental hand piece, a drill tip at the other end engageable with a root canal to facilitate drilling a bore in a tooth root, and a shaft extending between and integral with the hub and the drill tip, the shaft having a first step in diameter disposed between a first shaft portion having a first length and a second shaft portion having a second length, the first shaft portion extending between the hub and the first step, and the second shaft portion extending between the first step and the tip, the diameter of the first shaft portion at the first step being larger than the diameter of the second shaft portion at the first step, creating a first reduction in the diameter of the shaft in the direction toward the tip, the second shaft portion including a substantially straight root canal drilling section extending inwardly from the tip to an outermost bend in the second shaft portion defining a substantial outermost angle between the drilling section and the remainder of the second shaft portion, the first shaft portion including an innermost bend adjacent to the hub to dispose the section of the first shaft portion located between the innermost bend and the first step at an innermost angle relative to an imaginary extension of the longitudinal axis of the hub, the length of the first shaft portion being in the approximate range of about 60% to about 80% of the total length of the shaft and the length of the second shaft portion being in the approximate range of about 20% to about 40% of the length of the shaft.

2. The dental retro-filling preparation tool of claim 1 wherein the ratio of the first length to the second length is in the approximate range of about 1.5:1 to about 2.5:1.

3. The dental retro-filling preparation tool of claim 2 wherein the ratio of the first length to the second length is approximately 1.6:1.

4. The dental retro-filling preparation tool of claim 1 wherein the ratio of the first diameter to the second diameter is in the approximate range of about 3:1 to about 4:1.

5. The dental retro-filling preparation tool of claim 4 wherein the ratio of the first diameter to the second diameter is approximately 3.4:1.

6. The dental retro-filling preparation tool of claim 1 wherein the ratio of the first length to the second length is approximately 1.6:1 and the ratio of the first diameter to the second diameter is approximately 3.4:1.

7. The dental retro-filling preparation tool of claim 1 wherein the outermost angle is approximately 90°.

8. The dental retro-filling preparation tool of claim 1 wherein the outermost angle is substantially less than 90°.

9. The dental retro-filling preparation tool of claim 1 wherein the innermost angle and outermost angle are selected to dispose the substantially straight root canal drilling section approximately parallel to the longitudinal axis of the hub.

10. The dental retro-filling preparation tool of claim 9 wherein the innermost angle and the outermost angle are approximately equal.

11. The dental retro-filling preparation tool of claim 10 wherein the outermost and innermost angles are approximately 37°±2°.

12. The tool of claim 1 wherein said substantially straight root canal drilling section includes a second diameter step creating a second reduction in the shaft diameter in a direction toward the tip.

13. The tool of claim 12 wherein said substantially straight root canal drilling section includes a third diameter step located between the second diameter step and the tip creating a third reduction in the shaft diameter in the direction toward the tip.

14. The tool of claim 13 wherein the distance between the second and third steps is less than the distance between the third step and the tip.

15. The tool of claim 1 wherein the distance along the shaft between the tip and the first step is a minimum of approximately 0.2 inches.

16. The tool of claim 1 wherein the tool shaft is solid.

17. The tool of claim 1 wherein the distance between the first step and the hub is in the range of from about 0.5 inches to about 0.6 inches.

18. The tool of claim 1 wherein the overall length thereof is in the approximate range of about 1.2 inches to about 1.3 inches.

19. The tool of claim 1 wherein the hub has a diameter larger than the first diameter.

20. The tool of claim 1 wherein the substantially straight root canal drilling section is at an offset angle to the plane defined by said remainder of said second shaft section and the hub.

21. The tool of claim 20 wherein the offset angle is approximately 90°.

22. The tool of claim 1 or 2 or 3 or 4 or 5 or 6 in which the first shaft portion is tapered and in which the shaft sections located between the tip and each step are tapered.

23. A dental retro-filling preparation tool, comprising:

an elongate drill bit having a hub at one end, the hub having a longitudinal axis and a coupling formation for releasably connecting the hub to an ultrasonic transducer head, a tip at the opposite end to the hub for drilling into a tooth root, and a shaft extending from the hub to the tip, the shaft having at least one step in diameter at a predetermined position in its length;

the shaft having a first shaft portion extending from the hub to the step, the first shaft portion having a first diameter at least at the step, and a second shaft portion extending from the step to the tip, the second shaft portion being of diameter less than said first diameter along its length;

said first shaft portion including an outer section thereof which is inclined at an angle to the hub axis, and said second shaft portion having an outer substantially straight cutting section terminating at the tip which is angled relative to the remainder of the second shaft portion whereby said tip and cutting section are bent at an angle to said shaft; and said bent cutting section being co-planar with said hub and shaft.

24. A tool assembly for drilling a bore in a tooth root, comprising:

a set of different elongate drill tips for selectively securing to an ultrasonic transducer head;

each drill tip having a hub at one end having a coupling formation for releasable connection to a mating coupling formation on the transducer head, an opposite cutting end, and a shaft extending from the hub to the cutting end, the shaft having at least one step in diameter at a predetermined position in its length;

the shaft comprising a first shaft portion extending from the hub to the step and having a first diameter at least at said step, and a second shaft portion extending from said step to said cutting end, the diameter of said second shaft portion being less than said first diameter; and at least two of said drill tips comprising primary drill tips for use in initial drilling of a bore, the primary drill tips each having a shaft extending at a first angle to said hub and a bend adjacent said cutting end forming a bent end portion at a second angle to said shaft, a first primary drill tip having a bent end portion which is co-planar with said hub and shaft and a second primary drill tip having a bent end portion which is offset at a third angle to the plane of the hub and shaft.

25. The assembly as claimed in claim 24, wherein the first angle is between 35° and 39° and the second angle is between 88° and 92°.

26. The assembly as claimed in claim 25, wherein the third angle is 90°±2°.

27. The assembly as claimed in claim 24, including a third primary drill tip which has a bent end portion offset in the opposite direction to the bent end portion of said second primary drill tip.

28. The assembly as claimed in claim 27, wherein said second and third drill tips have bent end portions offset in opposite directions at an angle of 90° to the plane of the hub and shaft.

29. The assembly as claimed in claim 24, wherein one of said drilling tips has a flattened cutting end and the other drill tips all have pointed cutting ends.

30. The assembly as claimed in claim 24, including a drill tip for correcting offset bores having a shaft at a first angle to the hub and a bend forming a bent end portion at a fourth angle of greater than 90° to said shaft.

31. The assembly as claimed in claim 30, wherein the fourth angle is between 141° and 145°.

32. The assembly as claimed in claim 24, including an additional drill tip having a straight shaft up to said cutting end.

33. The assembly as claimed in claim 32, wherein the shaft of said additional drill tip is inclined at an angle to the hub axis.

34. The assembly as claimed in claim 33, wherein said additional drill tip is inclined at an angle in the range of 35° to 39°.

35. The assembly as claimed in claim 24, wherein the ratio between the diameter of the first shaft portion to the diameter of the second shaft portion is in the range from 3:1 to 4:1.

36. The tool as claimed in claim 35, wherein the ratio is 3.7:1.

37. The tool as claimed in claim 24, wherein the ratio between the length of the first shaft portion and the length of the second shaft portion is in the range from 1.5:1 to 2.5:1.

38. The tool as claimed in claim 24, wherein each drill tip has at least two steps in diameter comprising a first step at the end of said first shaft portion and a second step dividing said second shaft portion into a larger diameter part and a smaller diameter end part.

39. The tool as claimed in claim 38, wherein the bend is located in the larger diameter part of said second shaft portion.

* * * * *